(12) United States Patent
Machida

(10) Patent No.: US 6,426,149 B1
(45) Date of Patent: *Jul. 30, 2002

(54) CERAMIC STRUCTURE AND METHOD FOR MANUFACTURING THE STRUCTURE

(76) Inventor: Akitoshi Machida, 2-39-10 Bessho, Urawa, Saitama (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/921,498

(22) Filed: Sep. 2, 1997

(30) Foreign Application Priority Data

Sep. 3, 1996 (JP) .............................. 8-253890
Feb. 20, 1997 (JP) .............................. 9-051183

(51) Int. Cl.[7] .......................... B32B 17/06; A61C 13/08
(52) U.S. Cl. ...................... 428/434; 428/469; 428/472; 428/701; 428/702; 433/201.1; 433/207
(58) Field of Search ................. 428/434, 433, 428/469, 472, 701, 702; 433/201.1, 206, 207

(56) References Cited

U.S. PATENT DOCUMENTS

| 3,720,541 A | * | 3/1973 | King ........................... 428/434 |
| 4,229,170 A | * | 10/1980 | Perez ........................... 433/206 |
| 4,676,751 A | * | 6/1987 | Shoher et al. |
| 4,997,723 A | * | 3/1991 | Tanaka ........................... 428/606 |
| 5,032,429 A | * | 7/1991 | Diefenbach ................. 428/434 |
| 5,104,320 A | | 4/1992 | Stoll ........................... 433/206 |
| 5,186,626 A | * | 2/1993 | Tanaka |
| 5,783,310 A | * | 7/1998 | Sano ........................... 428/434 |

FOREIGN PATENT DOCUMENTS

| JP | 4-339700 | 11/1992 |
| JP | 5139871 | 6/1993 |

* cited by examiner

*Primary Examiner*—Deborah Jones
*Assistant Examiner*—Jennifer McNeil
(74) *Attorney, Agent, or Firm*—Norris, McLaughlin & Marcus P.A.

(57) ABSTRACT

A ceramic structure where a gold foil or a platinum foil having a high purity is enclosed between a first layer made of a ceramic material fused at a medium temperature or a glass material (glass substance) and a second layer made of a ceramic material fused at a low temperature and/or a glaze material, or made of a glaze material or fritting glass material. Since such a ceramic structure is light in weight and has excellent durability, the final product can be preferably applied to fashion accessories, ornaments on artificial teeth.

7 Claims, 3 Drawing Sheets

CERAMIC STRUCTURE AND METHOD FOR MANUFACTURING THE STRUCTURE

BACKGROUND OF THE INVENTION

1) Field of the Invention

The present invention relates to a ceramic structure, and particularly relates to a ceramic structure which is suitably used for fashion accessories, such as rings, pins; ornaments, such as wall hangers; glass products, such as glassware; or ornaments applied to the surface of artificial teeth.

2) Related Art

Ornamental products using gold or platinum materials, gold or platinum plates where a metal curving technique is applied, or glass plate on the surface of which ornamentally designed gold or platinum foil is attached, or ornaments where a designed gold or platinum foil is sandwiched between transparent glass plates are well known.

However, a large amount of gold or platinum is necessary to obtain the ornamental products made of gold or platinum material on which a metal curving technique is applied, so the cost for manufacturing the products becomes high. Further, these metal materials are comparatively soft so that the portions where the ornamental design is applied is apt to be deformed and the surface of these products is apt to crack.

Other ornamental products on which designed gold or platinum foil is fused and attached have problems in their durability because the foil peels when the products are used for a long time. Further, other products where a gold or platinum foil is sandwiched between transparent glass plates have the inconvenience of being thick and heavy.

Concerning ornaments applied on the surface of artificial teeth, many efforts are being paid to realize shape and color close to a natural tooth, however, ornamental designs on the surface of artificial teeth have not been yet.

In order to solve the problems of conventional techniques, the present inventor suggests a ceramic structure having two layers, i.e. a basic layer and a second layer where an ornamental designed gold foil is held between the layers in Japanese Patent Application No. 95-70329 and 95-264602. However, the generally used ceramic material requires a high temperature about 1300° C. to be burnt, and therefore, a glaze layer (the second layer) peels off from a basic layer or many cracks are caused in the glaze layer due to the difference in the coefficients of thermal expansion between the basic layer and the glaze layer (second layer). As a result, the gold foil or platinum foil sandwiched between the basic layer and the glaze layer is deformed.

SUMMARY OF THE INVENTION

The present invention has for its object to provide a thin and light ceramic structure having a plurality of layers between which an ornamental designed foil made of gold or platinum is arranged. According to the invention the brightness and the design of the foil made of gold or platinum can be kept as is for a long period without having any damage.

The present invention has another object to provide an artificial tooth on which an ornamental design is applied by using the ceramic structure according to the invention.

In order to solve the tasks, a ceramic structure according to the present invention comprises a first layer composed of a ceramic material which is fused at a medium temperature, a second layer composed of a ceramic material which is fused at a low temperature and/or a glaze material, and a gold and/or platinum material having a high purity being sealed between said first and second layers.

In this specification, the ceramic material fused at a medium temperature means a ceramic material which is burnt at a temperature of 920 to 960° C., more preferably about 940° C.; and the ceramic material fused at a low temperature means a ceramic material which is burnt at a temperature of 660 to 810° C., more preferably about 720 to 780° C. If the burning temperature of the second layer is higher than that of the first layer, the first ceramic layer, which works as a basic layer, is shrunk and then deformed, so that it becomes difficult to form the final products in a good manner. Then, in the first invention of the present application, a ceramic material which is fused at a medium temperature is used as a first layer and a ceramic material which is fused at a low temperature and/or a glaze material is used as a second layer, so that the temperature for burning the second layer (2nd burning) does not become higher than the temperature for burning the first layer (first burning) in order to prevent the deformation of the first layer. According to the present invention, the difference between the temperature at the first burning for the first layer and the temperature at the second burning for the layer becomes about 150 to 200° C. Therefore, the deformation of the first layer after burning the second layer could be completely prevented.

Further, it is preferred to use a ceramic material fused at a medium temperature used for the first layer, whose coefficient of thermal expansion is 102 to 152 ($\times 10^{-7}$/° C.). It should be noted that the structure according to the first invention can preferably be used to apply an ornamental design on the surface of the artificial tooth, where an accurate technique is required to manufacture it.

In the case that a ceramic material fused at a low temperature is used for the second layer, it is desired to burn the structure under a reduced pressure. Because air bubbles included inside of the ceramic material fused at a low temperature are removed by burning under reduced pressure, and thus the transparency of the second layer becomes better. The burning under a reduced pressure is conducted in a furnace having a degree of vacuum of about 720 to 760 mmHg. Further, it is desired that the gold or platinum used as a material for the ornamental designed foil has a purity of 98% or more, and includes 1% or less silver.

It may be possible to use only a glaze material, or a mixture of glaze material and a ceramic material fused at a lower temperature for the second layer. If the amount of glaze material is great, the fluid characteristic thereof becomes better and the surface of the final product then becomes smooth.

A ceramic structure according to the second invention comprises a first layer composed of a glass material or a glass substance, a second layer composed of a glaze material and/or a fritting glass material, and a gold and/or platinum material having a high purity being sealed between said first and second layers.

The conditions for fusing the glass material as the first (basic) layer and the glaze material or the fritting glass material as the second layer are:

(1) The coefficients of thermal expansion of both materials of the first and second layers are close together;

(2) The softening temperature of the glass material of the basic layer is matched to the melting temperature of the glaze material or the fritting glass of the second layer; and (3) Even if the glaze material or the fritting glass of the second layer is fully fused, the glass material of the basic layer is not fused.

Therefore, the glass material for the basic layer withstands burning at a temperature of 500–820° C. at which the glaze material or the fritting glass material of the second layer is completely fused; and the material should preferably have the coefficient of thermal expansion of 80 to 140 ($\times 10^{-7}$/° C.) where the measurement is conducted at a temperature of 25 to 450° C. Crystal glass, fusing glass or optical glass can suitably be used for the material of the basic layer of the ceramic structure according to the second invention. It should be noted that daily used glass products, such as eye glasses, or glassware can be used as the basic layer. Further, bowls or ornamental objects on which cloisonne are applied can preferably be used as the basic layer made of glass substance.

By using such a thermostable glass material for the basic layer, it can be prevented that the basic layer is deformed when the second burning is conducted to form the second layer made of the glaze material or fritting glass material. Therefore, according to the second invention, it becomes possible to enclose the ornamental designed foil made of gold or platinum on the surface of the basic layer which has a large surface. Further, when the coefficient of the thermal expansion of the second layer, i.e. the glaze material or the fritting glass material as the second layer is almost the same as the above mentioned coefficient of the thermal expansion of the basic layer, no crack is caused on the surface of the final products.

When the ornament is applied on the surface of glass products, such as glassware or eye glasses, it might be possible to conduct the second burning in a condition that only the portion where the gold or platinum foil is temporarily adhered is covered by the glaze material or the ceramic material fused at a low temperature.

The method for manufacturing the ceramic structure according to the first invention of the present application, has the following steps:

burning a ceramic material fused at medium temperature at a temperature of 920 to 960° C., preferably 940° C. to obtain a first layer (a basic layer)

arranging a foil made of gold and/or platinum on said first layer with a binding agent and heat it up until the temperature in a furnace becomes 750° C. to temporarily adhere said foil on the first layer;

applying a ceramic material fused at a low temperature and/or a glazing material on the surface of said first layer so as to cover at least an area where said foil is applied to obtain a second layer; and burning a structure having said first and second layers and said foil until the temperature in a furnace becomes at 760 to 810° C., more preferably at 780° C.

Furthermore, the method for manufacturing the ceramic structure according to the second invention of the present application, has the following steps:

preparing a first layer made of glass material or glass substance;

arranging a foil made of gold and/or platinum with a binding agent and heat it up until the temperature in a furnace becomes 720 to 780° C., more preferably 750° C. to temporarily adhere said foil on the first layer;

applying a ceramic material fused at a low temperature and/or a glazing material on the surface of said first layer so as to cover at least an area where said foil is applied to obtain a second layer; and burning a structure having said first and second layers and said foil until the temperature in a furnace becomes 760 to 820° C., more preferably 780° C.

Further, the ceramic structure according to the first invention of the present application can suitably be applied to accessories for artificial teeth. In this case, it is desired to use only a glaze material for dental use or a mixture of the glaze powder for dental use and a glazing material which includes no or only a little amount of Pb is used as the material for the second layer in order not to have a bad effect on the body.

DETAILED DESCRIPTION OF THE PREFERRED EMBODIMENTS

Figure 1A:
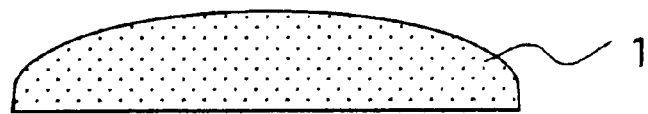
FIGS. 1(*a*) to 1(*d*) are cross sectional views showing steps for manufacturing a ceramic structure according to the first invention of the present application.
Figure 1B:
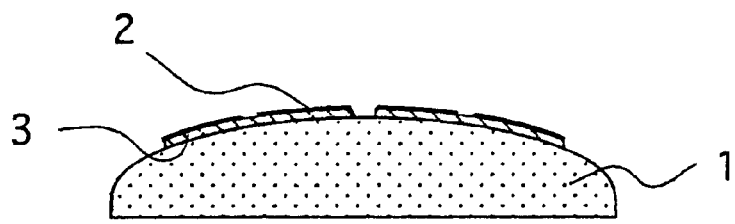
Figure 1C:
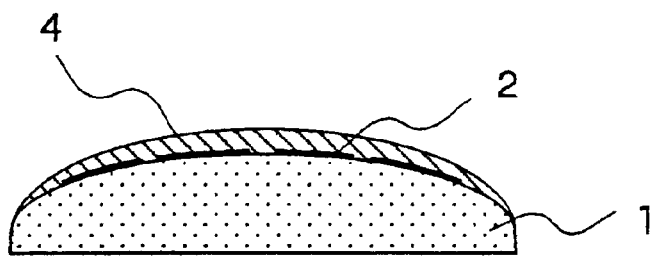
Figure 1D:
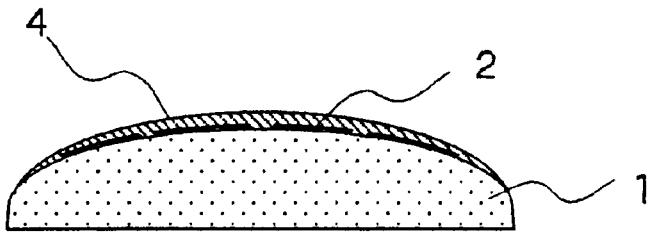
Figure 2:
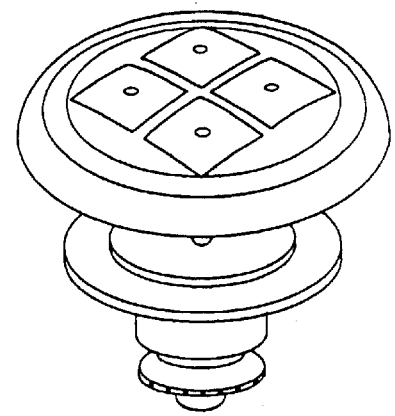
FIG. 2 is a schematic view depicting a final product in which a ceramic structure according to the first invention of the present application is applied.

The preferred embodiments of the ceramic structure and the manufacturing method of the structure according to the present invention will be explained below.

First Embodiment

The ceramic structure of the first embodiment according to the present invention has a feature that a ceramic material fused at a medium temperature is used as a first layer, a glaze material is used as a second layer and an ornamentally designed foil made of gold is enclosed between said first and second layers.

FIGS. 1(*a*) to 1(*d*) are cross-sectional views showing steps for manufacturing the ceramic structure according to the first invention. A ceramic material fused at a medium temperature, such as VITA 530 (name of a product produced by VITA co., LTD.) and Unibond (name of a produce produced by SHOFU CO., LTD.), was prepared as a starting material of the first layer, and put in a molding pattern which has a given shape. Then the ceramic material was condensed and water contained in the material was drawn by sucking, and then burnt in a furnace until the temperature of the furnace becomes 920 to 940° C. (first burning) to obtain a base 1 (first layer).

Then, the surface of the base 1 is treated by rubbing with the aid of a sand paper in order to have a condition to put the ornamental designed foil there easily. The thus treated base is washed out with water; an ornamentally designed foil 2 made of gold is arranged thereon via an binding agent 3; and then the base and the foil 2 are heated up until the temperature of the furnace becomes 760° C. in order to temporarily adhere the foil 2 on the surface of the base layer. It is desired to use a gold foil having a thickness of about 0.5 to 1 m. Further, a highly purified gold foil, such as a gold foil for use in dental treatment whose purity is about 99.99%, and which includes only a little amount of silver, i.e. 1% or less, should be used, otherwise the brightness of the gold would be reduced due to the vaporization of the silver contained in the gold. The desired ornamental design of such a thin foil made of gold could be obtained by using a cutting die, a cutting tool, or a laser cutting technique. It may be possible to obtain the designed gold on the first layer by putting a binding agent so as to form a desired design on the basic layer 1 and then spraying gold powder thereon.

It should be noted that the binding agent for temporarily attaching the gold foil on the basic layer should disappear. That means it is required to use a binding agent that has a feature that no residue is left after the temporary burning at a temperature of 500 to 750° C. is finished. CMC (Carboxymethylcellulose) paste or funorin can be preferably used for this purpose.

The binding agent functions to surely adhere the metal foil on the basic layer and to prevent that when the second layer is formed the foil peels off from the basic layer or bubbles formed are left between the basic layer and the gold foil. If the residue of the binding agent is still left on the base after the first burning is conducted, not only the transparency of the product after the second layer is formed thereon becomes worse but also the surrounding of the ornamentally designed gold foil becomes dark, so the brightness of the gold would be lost. According to the present invention, the burning for temporarily attaching the gold foil 2 on the first layer 1 is conducted at a temperature of 700° C. or more in order to burn the paste enough so that such a problem is not caused.

Then, the material for the second layer, i.e. white transparent glaze which is fused at a low temperature, is applied on the basic layer so as to cover the ornamentally designed gold foil which adhered on the first layer, and then burnt until the temperature in the furnace becomes 780° C. (second burning) to obtain the second layer 4. The thickness of the material for the second layer 4 should be 1 mm or less, more desirably about 0.2 to 0.5 mm and should be applied in a uniform manner. It should be noted that a mixture of the ceramic material fused at a lower temperature and the white transparent glaze may be possible to use for the material of the second layer 4. Particularly, Duceram LFC (name of the product by Ducera Co., Ltd.) has an excellent transparency and can preferably be used for the material of the second layer 4.

In the ceramic structure obtained in such a manner, it is possible to seal the ornamentally designed gold foil enclosed between the ceramic material (first layer) and the glaze material (second layer) without getting the foil out of shape. According to this embodiment, a ceramic material fused at a medium temperature is used for the first layer 1; and the first layer 1 is burnt at a comparatively high temperature, i.e. about 940° C.; the glaze layer (second layer) 4 is burnt at a temperature 150 to 200° C. lower than the temperature for burning the first layer 1. Therefore, the first layer is not deformed when the second layer is burnt, so that the desired formation of the final product can very easily be obtained.

The ceramic material for use in the basic layer which is fused at a medium temperature, has a structural feature that a crystal and feldspar are bonded together so as to surround a leucite ($K_2O$, $Al_2O_3$, $4SiO_2$) (crystal phase). Therefore, the first layer is apt to be mechanically and chemically bonded with the glaze layer (second layer) by means of the glass layer of the glaze material. Thus, it is possible to bond these layers together even if the coefficients of the thermal expansion of these materials are different to some degree from each other. It means general ceramic material having the coefficient of thermal expansion of 102 to $152 \times 10^{-7}/°$ C., more preferably $135 \times 10^{-7}/°$ C., which is produced by general manufactures, can be used. It should be noted that the coefficient of the thermal expansion of the white transparent glaze, which is used as the material for the second layer, is $(104 \pm 10) \times 10^{-7}/°$ C.

Figure 3:
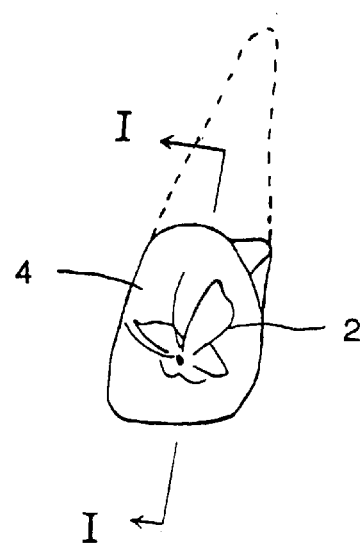
FIG. 3 is a schematic view illustrating an artificial tooth on which a ceramic structure according to the first invention of the present application is applied.
Figure 4:
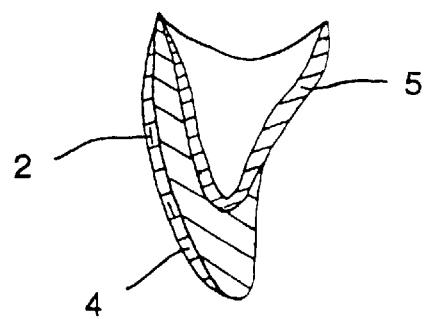
FIG. 4 is a cross sectional view of the artificial tooth illustrated in FIG. 3.

The structure according to the first invention of the present application can be preferably used to apply an ornamental design on the surface of an artificial tooth. FIGS. 3 and 4 are schematic views showing an example of such an artificial tooth on which an ornamental design is applied in accordance to the first invention. As is well known, an accurate technique is required to manufacture an artificial tooth. In case that an ornament is apply on the surface of such an artificial tooth, the following procedure is taken. A refractory mold of a tooth, which is obtained from a user, is prepared first; a ceramic material fused at a medium temperature is put on the mold and the first burning is conducted to obtain a base having a shape of a tooth; then the ornamentally designed gold foil is enclosed between the base and the second layer in accordance with the steps explained above. Then the thus obtained ceramic structure, which has a designed gold foil inside, is attached on the tooth of the user with the aid of boding agent for dental use. Instead of the base, artificial tooth, such as laminate benia or porcelain jacket, or metal-baked porcelain, and denture, which are generally used for the dental treatment, can be preferably used as the first layer. Such an ornament can be applied on all over the front surface of the tooth or only on a part of the front surface.

(Second Embodiment)

Figure 5:
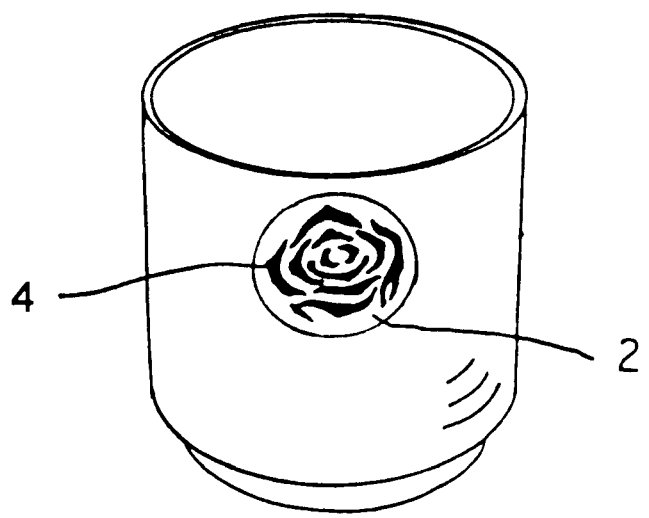
FIG. 5 is a schematic view representing a final product on which a ceramic structure according to the second invention of the present application is applied.
Figure 6:
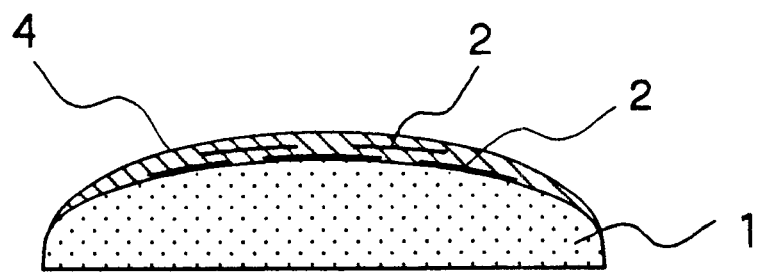
FIG. 6 is a cross sectional view showing a modification of a ceramic structure according to the first invention of the present application.

According to the second embodiment of the present application a glass plate is used as the first layer. That is to say, a foil made of gold is temporarily attached on a glass plate, then a fritting glass material or glaze material is applied thereon so as to cover the foil; the materials are burnt to enclose the gold foil between the glass plate and fritting layer or the glaze layer. In the second embodiment, the final product is a glassware, on the thin surface of which a gold foil is enclosed. FIG. 5 is a schematic view illustrating the glassware as the final product.

A rough sketch is drawn on the surface of the glassware made of a crystal glass having its coefficient of thermal expansion of about 104 and its softening point of 646° C.; and the CMC paste is applied on the roughly sketched portion in a thin and uniform manner; a gold foil is applied on the rough sketch; burning it at a temperature of about 600° C. in order to burn out the CMC paste; then to cool it down slowly. If some residue of the binding agent is left, which makes the brightness of the gold foil and the transparency of the glass material worse, it should be removed carefully. After the crystal glass with the gold foil is sufficiently dried, the portion where the ornament is not necessary is covered with a mask film; and then spraying a fritting glass mixed with water so as to cover the designed portion. In this embodiment, a transparent fritting glass fused at an extremely low temperature having a coefficient of thermal expansion of about $104 \times 10^{-7}/°$ C. and a softening point of about 380° C. is used as the second layer. If the glass used as the basic layer is pre-heated, the sprayed fritting glass material would get dry fast, so it can be prevented the fritting material overflows and a uniform thickness can be obtained on the fritting glass layer. The product is then heated up 600 to 620° C. in an electric furnace, and kept at the temperature of 600° C. for 2 or 3 minutes; then the product is taken from the furnace to gradually cool down.

In the case that thick crystal glassware is used as the base, a fritting glass material, which is fused at an extremely low temperature, is used for the second layer and the burning is conducted at a temperature of 600 to 650° C., and then the product is gradually cooled down. In this case, the paste should be burn out at the temperature of about 750° C.

The difference in the coefficient of the thermal expansion between the crystal glass material of the basic layer and the glaze material and/or fritting glass material of the second layer should be under $7\times10^{-7}/°$ C. In the above-mentioned second embodiment, the fritting glass material is applied by spraying, however brushing or screen printing can be used instead. It is desired to arrange the thickness of the fritting glass layer, i.e. the second layer, about 0.2 to 1 mm. The reason is, if the thickness is greater than this, the fritting glass material would overflow due to its high flowability thereof. Further, in the second embodiment, the mixture of the fritting glass and water is used as the material of the second layer, but organic binder can be mixed with the fritting glass instead of water.

A crystal glass having the coefficient of the thermal expansion of $104.5\times10^{-7}/°$ C. and the softening point of 646° C., soda-lime glass having the coefficient of the thermal expansion coefficient of $104\times10^{-7}/°$ C. and the softening point of 696° C., or an optical glass having the coefficient of the thermal expansion coefficient of $95.8\times10^{-7}/°$ C. and the softening point of 722° C. are able to be preferably used as a basic glass material. Colored glass can also be used as well as the transparent glass. Other glass material can also be used as long as the material satisfies the condition of the coefficient of a thermal expansion of 80 to $140\times10^{-7}/°$ C. and a softening point of 500° C. or more, and the difference in the coefficient of the thermal expansion between the glass material for the first layer and the material for the second layer, i.e. fritting glass or glaze, is small.

It is not necessary that the surface of the base is flat. That is to say, the gold foil can be enclosed on, for instance, the curved surface of eye glasses, or a glassware.

In the first and second embodiments, there are provided three layers, i.e. the first layer, gold foil and the second layer. However, after the gold foil is enclosed between the first and the second layers, another gold foil and a third layer made of ceramic material or a mixture of the ceramic material and a glaze material can be formed by using the same procedure as mentioned above so as to obtain multiple layered ornaments.

As explained above, according to the present invention, the brightness of the ornamentally designed foil made of gold or platinum enclosed between the first and the second layers can be kept well for long time period in a good condition. Further, even the foil is designed so finely, it is possible to seal it in the structure without damaging the design. According to the invention, the foil is never peeled off and the surface of the structure is not deformed, the product could have an excellent durability and the design can be kept for long time. Furthermore, since a ceramic material is used as the basic layer, the weight of the final product becomes light and the thickness significantly thin. Such a ceramic structure can be preferably used as fashion accessories. Further, since ceramic material can keep excellent chemical stability in the mouth, the invention can be applied as accessories for teeth.

What is claimed is:

1. A ceramic structure, comprising:

a first layer comprising a first ceramic material;

a second layer comprising at least one or both of a second ceramic material and a glaze material, said second layer having a lower fusing temperature than that of said first ceramic material; and a third layer being enclosed between said first layer and said second layer, said third layer being at least one of gold or platinum having a purity of 98 weight percent or more, wherein the content of silver therein is less than or equal to 1 weight percent.

2. A ceramic structure according to claim 1, wherein said third layer has a thickness of 0.5 to 1 micron.

3. A ceramic structure according to claim 2, wherein said first layer has the shape of a tooth.

4. A ceramic structure according to claim 2, wherein said third layer is enclosed in a multiple-layered manner.

5. A ceramic structure, comprising:

a first layer comprising a glass material or a glass substance;

a second layer comprising at least one or both of a glaze material and a fritting glass material, the second layer having a lower fusing temperature than that of said first layer; and a third layer being enclosed between said first layer and said second layer, said third layer being at least one of gold or platinum having a purity of 98 weight percent or more, wherein the content of silver therein is less than or equal to 1 weight percent.

6. A ceramic structure according to claim 5, wherein said third layer has a thickness of 0.5 to 1 micron.

7. A ceramic structure according to claim 6, wherein said third layer is enclosed in a multiple layered manner.

* * * * *